United States Patent [19]

Parks

[11] Patent Number: 4,685,901
[45] Date of Patent: Aug. 11, 1987

[54] GASTRO-JEJUNAL FEEDING DEVICE

[75] Inventor: Stephen K. Parks, San Jose, Calif.

[73] Assignee: Medical Innovations Corporation, Milpitas, Calif.

[21] Appl. No.: 795,163

[22] Filed: Nov. 5, 1985

Related U.S. Application Data

[63] Continuation-in-part of Ser. No. 670,381, Nov. 5, 1984.

[51] Int. Cl.$^4$ .................................................. A61M 25/00
[52] U.S. Cl. ........................................... 604/96; 604/178
[58] Field of Search ............... 604/97, 96, 104, 174, 604/175, 178, 180, 280; 128/DIG. 26

[56] References Cited

U.S. PATENT DOCUMENTS

| | | | |
|---|---|---|---|
| 3,144,868 | 8/1964 | Tascalevich | 604/93 |
| 3,253,594 | 5/1966 | Matthews et al. | 604/178 X |
| 3,915,171 | 10/1975 | Shermata | 604/104 X |
| 4,089,337 | 5/1978 | Kronner | 604/178 X |
| 4,114,625 | 9/1978 | Onat | 604/96 |
| 4,392,855 | 7/1983 | Oreopoulos | 604/174 |
| 4,393,873 | 7/1983 | Nawash et al. | 604/174 X |
| 4,516,968 | 5/1985 | Marshall | 604/174 |
| 4,543,089 | 9/1985 | Moss | 604/93 |

OTHER PUBLICATIONS

Moss, "Efficient Gastroduodenal Decompression with Simultaneous Full Interal Nutrition; a New Gastrostomy Catheter Technique", Journal of Parenteral and Enteral Nutrition, vol. 8, No. 2, 3/14/84, pp. 203-207.

*Primary Examiner*—Stephen C. Pellegrino
*Attorney, Agent, or Firm*—Willie Krawitz

[57] ABSTRACT

A device is disclosed for supplying food and medication to a patient, the device being inserted through a stoma and into the patient's stomach for feeding into the stomach and/or the jejunum. The device may also be used to feed directly into the jejunum by by-passing the stomach.

The device is secured in place by an inflatable balloon within the stomach, or by a plate if the stomach is by-passed, and by an adjustable ring on the abdominal wall. The adjustable ring also prevents ingestion of the device into the stomach. During use, the ring can be retracted to permit cleaning of the stoma area. The ring can be perforated and ribbed to provide improved ventilation of the stoma area during use.

The device can be employed with conventional surgically formed procedures, and is replaceable. Servicing of the device can be made at home, rather than at a hospital.

12 Claims, 7 Drawing Figures

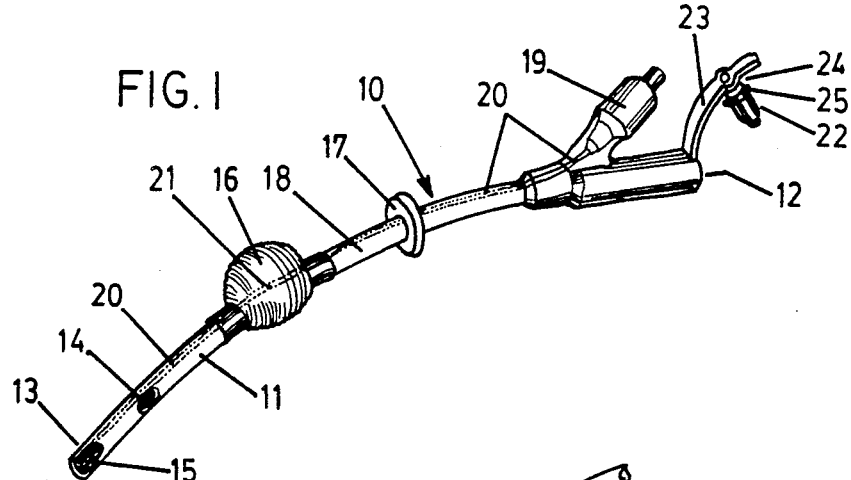
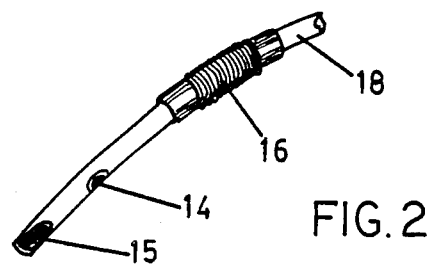
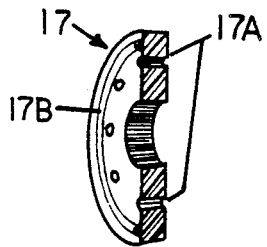
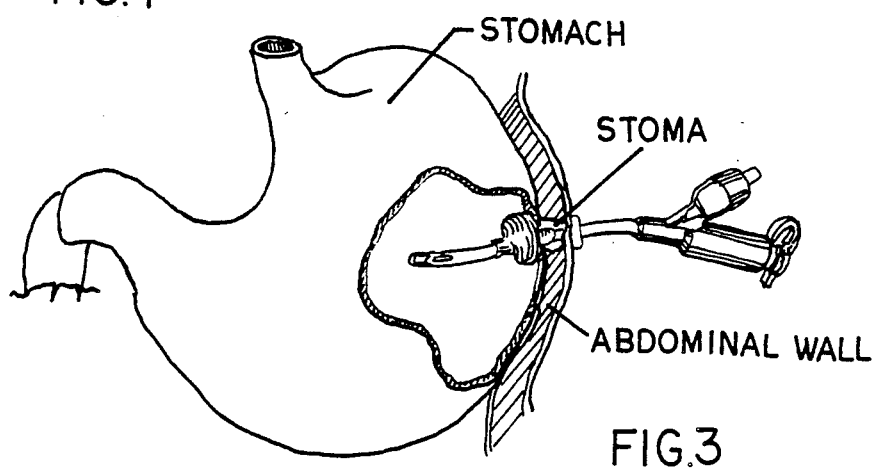

4,685,901

GASTRO-JEJUNAL FEEDING DEVICE

BACKGROUND OF THE INVENTION

This invention is a continuation-in-part of U.S. Ser. No. 670,381, filed on Nov. 5, 1984, and entitled: "Gastrostomy Feeding Device".

This invention relates to a new and improved feeding tube, and more specifically to a gastro-jejunal feeding tube that is insertable through a stoma in the patient's stomach wall and secured within the patient's stomach and against the abdominal wall. Alternatively, the device may be employed to by-pass the stomach and feed directly into the jejunum.

Some types of patient feeding devices employ a gastrostomy feeding tube. However, if the patient has a problem with gastric reflux or vomiting, or if the stomach is not adequate for the patient's digestive process requirements, another feeding mode must be chosen. This can be accomplished by by-passing the stomach and supplying food directly into the jejunum with a feeding tube.

Many types of feeding devices have been developed, but they suffer from various drawbacks. These include: the ejection or loss of liquids from the stomach and back out through the device; leaking around the periphery of the device; and, premature deterioration of the materials of construction. Also, it is difficult to maintain the device in place in a stable manner in the patient, and this latter problem can result in the device being ingested into the stomach, and eventually into the pylorum. Devices presently on the market are not sized properly, and they use materials that are prone to fairly rapid deterioration. Moreover, they can become entangled and dislodged from the patient due to improper sizing and inadequate locking of the device to the patient. In some prior art devices, the exterior of the gastrostomy tube is taped to the wearer's body. This procedure can cause infection at the stoma entry, and along the taped area, as well as causing irritation due to the difficulty in maintaining these areas clean.

Other prior art devices employ a spring biased or threaded locking mechanism to secure a locking ring to the wearer's body, the locking ring being fastened on the gastrostomy tube. But these devices maintain a fixed pressure or position of the locking ring on the gastrostomy tube, and do not self adjust to peristaltic pressure of the stomach. This is of particular importance in the case of neonatal patients or other such as incoherent or unconscious patients who are unable to communicate the nature of their discomfort.

THE INVENTION

According to the invention, a gastrostomy or jejunostomy feeding tube is provided for insertion through the stoma of the patient's stomach wall and into the patient's stomach and/or jejunum. The feeding tube is provided with an inflatable balloon at one end to position and secure the tube within the stomach. The outer end of the tube is provided with a moveable locking ring that can be adjusted by frictional engagement of the locking ring with the gastrostomy or jejunal feeding tube to accommodate to the size of the wearer. Since the locking ring does not require or employ tape to secure the device in place, problems associated with skin irritation and with maintaining both the taped areas and the stoma area clean are greatly reduced. The locking ring can simply be moved along the tube against the frictional force between the ring and the tube to permit cleaning of the stoma entry through which the catheter is inserted. The locking ring is then repositioned to its normal location, i.e., in close contact with the wearer's abdomen.

The balloon and locking ring thus both function to maintain the device in place, and prevent the device, by frictional engagement between the locking ring and tube, from being drawn into the stomach, or being inadvertently pulled out.

In the case of a gastro-jejunal feeding system, one embodiment of the invention involves extending the tube through the stomach and feeding directly into the jejunum. In another embodiment, the feeding system of this invention permits liquid food to be supplied to the jejunum while the stomach is drained by means of a comounted gastrostomy tube. This represents a significant benefit for patients who have a problem with gastric reflux or vomiting. However, if the stomach function is only somewhat impaired and vomiting or gastric reflux are not a problem with a particular patient, liquid food can be supplied to both the jejunum and the stomach through both tubes.

In another embodiment, the device may be adapted to feed directly through a jejunal stoma and into the jejunum.

The device of this invention is preferably constructed of a medical grade silicone elastomer, rather than a latex or silicone latex combination. Consequently, use of the silicone elastomer provides a suitably inert material compared to the latex. Hence, the elastomer requires replacement about every 6-8 weeks compared to a silicone latex which needs replacing about every three weeks.

BRIEF DESCRIPTION OF THE DRAWINGS

FIG. 1 is an external perspective view of the gastrostomy device of this invention;

FIG. 2 is an external perspective view of the said device partly fragmented, showing the outlet end, and the balloon when deflated;

FIG. 3 is a perspective view, partly broken away, of the said device installed in a patient;

FIG. 4 is an external perspective view of a preferred form of locking ring employed in the device;

DESCRIPTION OF THE PREFERRED EMBODIMENTS

Figure 5:
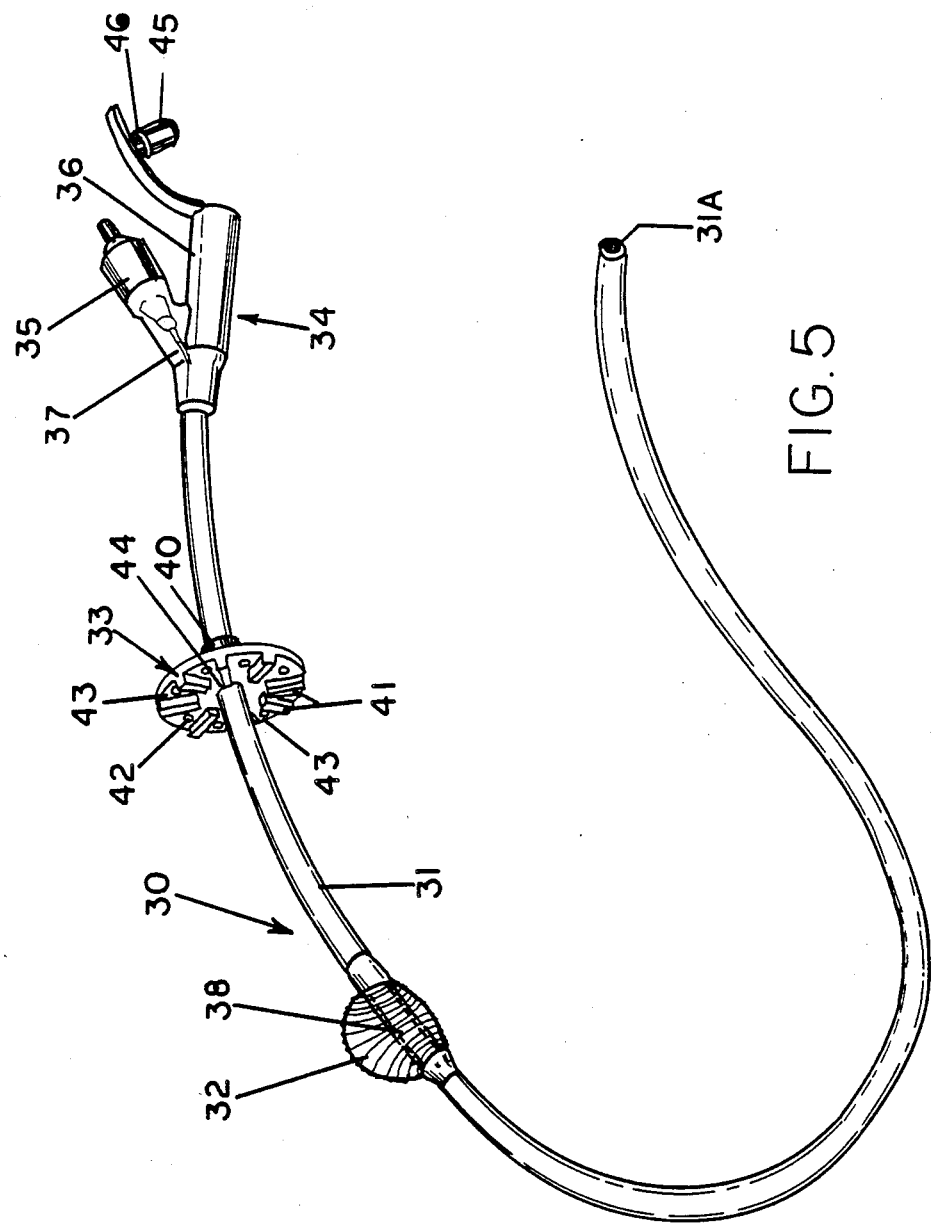
FIG. 5 is an external, perspective view of the said device for feeding into the jejunum via a stomach placed stoma.

The gastrostomy catheter device 10 of this invention is shown in FIG. 1, and provides an inlet end 12, through which is fed food and medication, and an outlet end 13 that extends into the patient's stomach. A plurality of outlet ports, two of which are shown, and located at the outlet end 13. The catheter 10 is secured inside the stomach by an inflatable balloon 16, and on the patient's abdomen by an adjustable silicone locking ring 17. As shown in FIG. 4, the locking ring 17 is provided with a plurality of vent holes 17A and a circular ridge 17B to permit air to contact the entry to the stoma and reduce infection and skin irritation.

As indicated, use of the ring prevents the catheter from being drawn into the patient's stomach. In addition, since the adjustable ring does not require the use of tape, a potential source of skin irritation and infection is eliminated. The portion 18 of the catheter tube 11 between the ring 17 and balloon 16 is secured within the stoma, and this arrangement of the balloon and ring prevents the catheter from being drawn into the patient's stomach.

In FIG. 1, the balloon is inflated by liquid or gas which is passed through a valve 19 and line 20 into port 21 that is surrounded by the balloon. The line 20 is bonded along the inside of the catheter tube 11 and extends to the outlet of the catheter where it is end sealed; the end seal forces the inflating gas into the port 21. FIG. 2 shows the balloon 16 in a deflated position.

The inlet end 12 is provided with an integrally formed end plug 22 attached to the catheter by a band 23. A plurality of rings 24, 25 are formed on the plug to engage corresponding frooves (not shown) on the inside of the bore at the inlet. The combined effect of the plug and bore fit, and the fit between the grooves and rings prevent the plug from being dislodged during use, and hence, will prevent the contents of the stomach from draining out the catheter.

Basically, the catheter device is inserted into the patient through a surgically prepared stoma created in the abdominal wall using pre-existing surgical procedures. These procedures include Stamms Gastrostomy, Witzel Gastrostomy, and others. Also, non surgical procedures may be employed such as percutaneous gastrostomy. The Janeway surgical procedure also may be used.

The catheter tube 10, with surrounding, concentric purse string sutures, is inserted through the stoma and gastric wall into the stomach. The purse strings will permanently invaginate a portion of the stomach and stoma to shape around the catheter tube and then will dissolve, leaving the gastrostomy tube in place and ready for use. FIG. 3 shows the device when installed. The inflated balloon forms a gasket that seals the entrance to the stoma, and along with the locking ring 17, secures the device in place. The device may be constructed in various sizes to accommodate a particular patient. Sizes such as 12, 14, 16, 18 and 20 French, and corresponding diameters varying from about 0.157"–0.263", and a wall thickness of about 0.034", may be used.

After being used for a suitable time, say 6-8 weeks, the catheter tube is, of course, replaced. This is accomplished simply by deflating the balloon, retracting the adjustable ring, and removing the tube.

Figure 6:
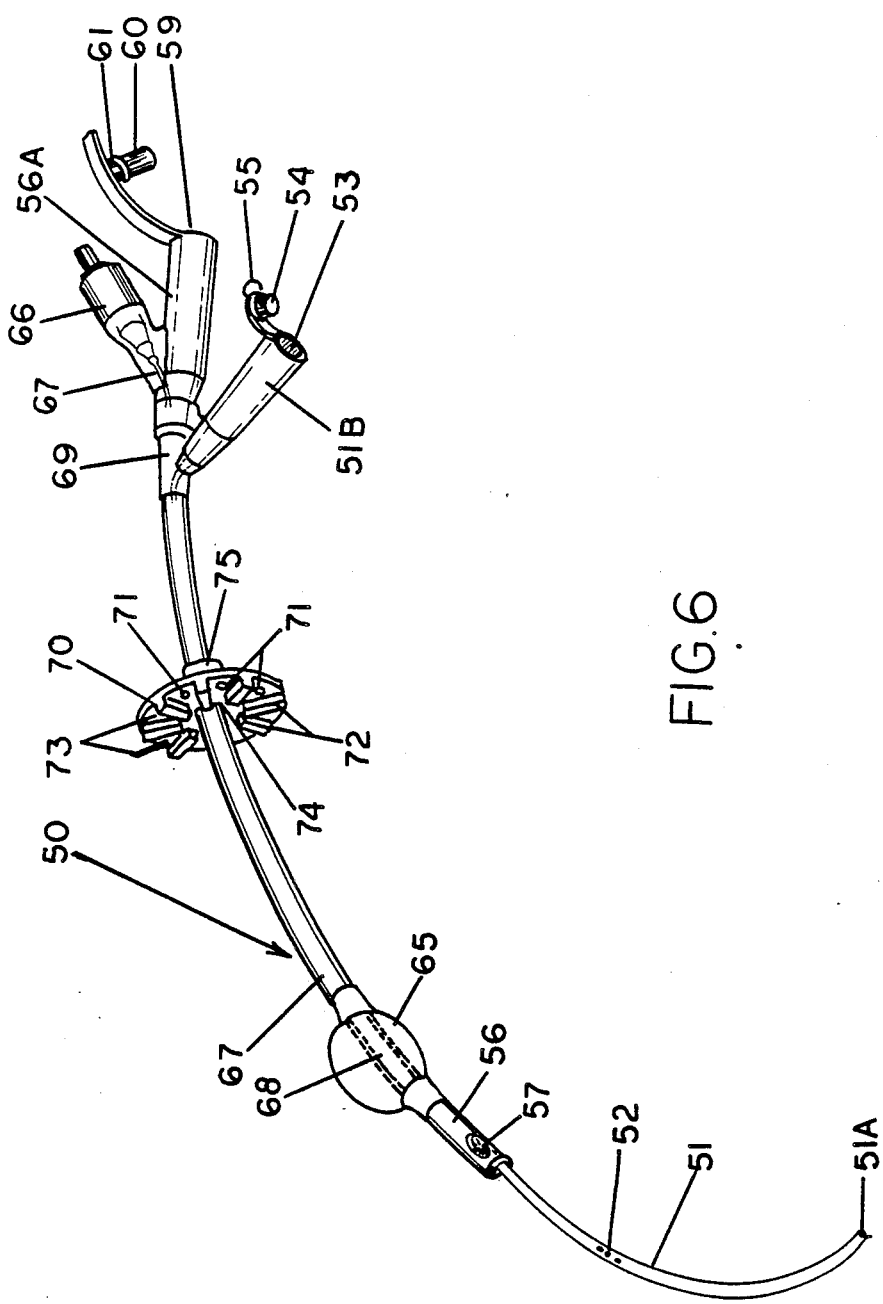
FIG. 6 is an external, perspective view of the said device for feeding into both the stomach and jejunum via a stomach placed stoma; and, FIG. 7 is an external, perspective view of the said device adapted for by-passing the stomach and feeding directly into the jejunum.
Figure 7:
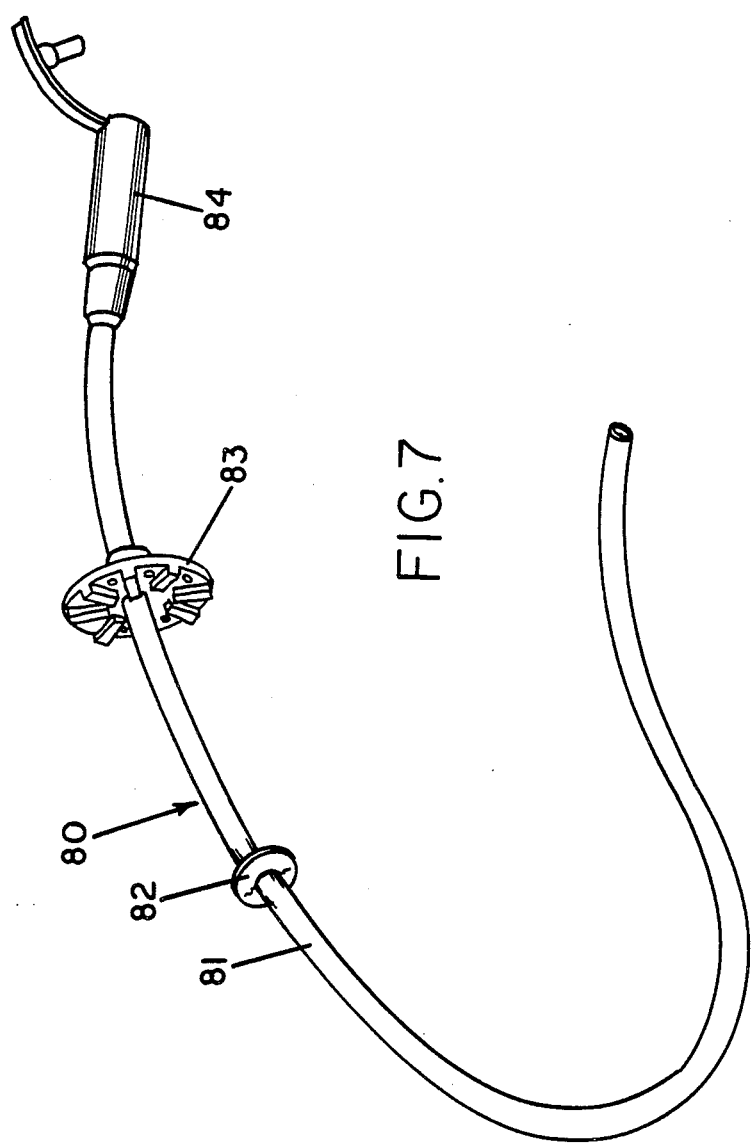

FIGS. 5 and 6 illustrate the use of a gastrostomy placed stoma for feeding into the jejunum (FIG. 5), or into the stomach and/or the jejunum (FIG. 6). FIG. 7 illustrates the use of a jejunal placed stoma which bypasses the stomach and feeds directly into the jejunum.

In FIG. 5, the jejunal feeding device 30 includes a feeding tube 31 having an open end 31a that extends through the stomach and into the jejunum. The device provides an expandable ballooe portion 32, locking ring 33 and an end member 34 having an inflating valve 35 and feed inlet 36. A gas line 37 is bonded along the interior of the tube and joins the interior of the balloon with the valve. An outlet port 38 enables the balloon to be filled from the valve via the gas line.

The locking ring 33 includes a collar 40 and a plurality of raised, concentric legs 41, air vents 42, and air gaps 43 between the legs to permit circulation of air between the ring and stoma area. The central portion of the locking ring defines a bore 44 through which passes the feeding tube 31. The frictional contact between the bore wall and collar 40 with the tube is sufficiently great to permit the locking ring to remain in contact with the patient's abdominal wall during use. However, the frictional contact between the tube and locking ring is sufficiently low so as to permit outward movement of the locking ring from the patient if the peristaltic pressure of the stomach becomes too great. Also, the frictional contact between the locking ring 33 and tube is sufficiently low to permit the locking ring to be moved away from the abdominal wall and enable the stoma area to be cleaned.

As in FIG. 1, the feed inlet 36 includes an attached cover plug 45 which can be inserted into the inlet and remain in place by means of a ring 46 that engages a corresponding groove (not shown) on the inside of the bore at the inlet.

The jejunal feeding tube 30 is inserted into the patient in the same manner as for the gastrostomy tube shown in FIG. 1. Since the jejunal tube is about 2 feet longer than the gastrostomy tube, it can be fed directly into the jejunum through a simple gastrostomy stoma.

The embodiments shown in FIGS. 5 and 6 represent a considerable advantage to a patient who has a problem with gastric reflux or vomiting, but does not require gstric decompression or drainage. In FIG. 6, the jejunal feeding tube device 50 includes a jejunal feeding tube 51, having an outlet end portion 51a which extends through the stomach into the jejunum, and which is perforated 52 to permit liquid food to be passed therethrough. The tube 51 connects at its inlet end 51b to a food inlet port 53 having a connecting plug cover 54 bearing one or more circular ridges 55. The plug cover can be inserted into the inlet port and will be secured therein by corresponding grooves (not shown) that engage the ridges 55.

Surrounding the feeding tube 51 is a shorter length gastrostomy tube 56 having a plurality of drainage inlets or food outlet ports, one such port 57 being shown. The drainage outlet (or food inlet) end 56a is enlarged to form a port 59 having an attached cover plug 60. One or more circular ridges 61 formed on the plug engages corresponding grooves (not shown) on the inside of the entry port to ensure a tight fit when the entry port 59 is closed.

An inflatable balloon 65 is provided near the end of the gastrostomy tube and is inflatable through a valve 66 bonded into the drainage (or inlet) end 56a. The valve is used to supply air to the balloon through a connecting line 67 and outlet port 68 under the balloon.

A connector 69 is employed to join the jejunum tube 51, inlet end 51b, gastrostomy tube 56, and drainage (or feeding) end 56a into a rigid package.

An adjustable, silicone locking ring 70 is provided with a plurality of vent holes 71 to permit air to contact the entry to the stoma and reduce infection and skin irritation. This is aided by a series of concentric lets 72 being spaced 73 for circulation of air therebetween. The central portion of the locking ring defines a bore 74 through which pass the jejunal and gastrostomy tubes 51 and 56. Frictional contact between the bore 74 and collar 75 with the gastrostomy tube 56 is sufficiently great to permit the locking ring to remain in contact with the patient's abdominal wall during use. However, the frictional contact between the tube and locking ring is sufficiently low so as to permit outward movement of the locking ring from the patient if the peristaltic pressure of the stomach becomes too great. Also the frictional contact between the locking ring 70 is sufficiently low to enable the locking ring to be retracted from the abdominal wall and permit the stoma area to be cleaned. As in FIG. 5, the already existing stoma can serve either as an entry for a jejunal tube or for a gastrostomy tube without any additional surgery being required.

In FIG. 7, use of an inflatable balloon is eliminated, and a plate is employed instead. The jejunum feeding device 80 is shown providing a jejunal tube 81, retaining plate 82, locking ring 83 and food inlet 84. The device is secured permanently by means of the plate 82 constructed of say a silicon material, which presses against the entrance to the stoma on the inside of the jejunal wall, and by the locking ring 83 which is pressed against the wearer's abdomen at the stoma entry. As in the other embodiments, the extent of frictional engagement between the locking ring 83 and the tube 81 is sufficient to prevent the device form being drawn into the user by peristalsis, while still enabling the ring to move outwardly due to expansion, or to be retracted so that the stoma may be cleaned.

The present device is inexpensive and can be readily manufactured by conventional extrusion and injection molding techniques. Also, it can be easily inserted for use without generally requiring the services of a physician or even outpatient services.

The device may be cleaned during use and can be manipulated to permit cleaning of the stoma area. Finally, the device is safe in that it cannot be drawn into the user, which can be particularly dangerous to unsuspecting infants and incoherent or unconscious patients, and the like. During use, it will not inadvertantly drain the contents of the stomach or jejunum because of the end plug.

I claim:

1. A device for feeding into a patient's jejunum, comprising:
   a. an elongate, jejunal feeding tube, including an outer extension from the patient's stomach, the tube having a feeding inlet end mounted on the outer extension and a perforated outlet end positioned within the patient's stomach;
   b. an inflatable balloon structure mounted around the tube and positioned near the outlet end of the tube;
   c. an inflation valve mounted near the inlet end of the tube;
   d. a valve line connected to the valve and providing an outlet port within the balloon structure, the valve line being positioned adjacent the feeding tube;
   e. a closure plug for the feeding inlet and secured to the feeding tube by an integral band; and,
   f. a locking ring positioned medially along the outer extension of the tube, and sized to frictionally engage the tube and slidably mounted therealong, and adjustable solely by frictional engagement with the tube to accommodate to the size of the wearer, the locking ring providing a plurality of perforations and spaced ridges to enable air circulation between the locking ring and patient's body; whereby,
      i. when the balloon is deflated, the feeding tube may be inserted through a stomach placed stoma and into the patient's jejunum;
      ii. when the balloon is inflated through the valve and valve line, it will secure the device within the patient's stomach and form a seal adjacent the stoma;
      iii. securement of the ring to the tube being provided solely by frictional engagement therebetween, to secure the device within the patient's body and to prevent undesirable movement of the ring along the tube, whether in the dry state or when lubricated by body fluids, the locking ring being manually adjustable along the tube to accommodate to the size of the patient, and the balloon and ring both functioning to maintain the device in place in the patient;
      iv. retraction of the ring being entirely against the force of frictional engagement to enable the stoma and adjacent areas to be cleaned; and,
      v. when the balloon is deflated, retraction of the ring enables the device to be removed from the patient.

2. The device of claim 1, which provides a gastrostomy tube surrounding the jejunal tube, the balloon and locking ring being mounted on the gastrostomy tube, the gastrostomy tube including a feeding inlet and closure plug therefor, the gastrostomy tube being adapted to feed and drain the stomach.

3. The device of claim 2, comprising a connector for securing the jejunal tube and gastrostomy tube and their respective inlet ends.

4. The device of claim 1, constructed of a medical grade silicone elastomer, and the like.

5. The device of claim 1, in which the spaced ridges of the locking ring are arranged radially of the ring.

6. A method for jejunal feeding, comprising:
   a. inserting a jejunal tube through a stomach placed stoma and into a patient's jejunum; and,
   b. supplying food through the tube to the patient's jejunum, the said tube comprising:
      1. an elongate feeding tube, including an outer extension from the patient's stomach, the tube having a feeding inlet and mounted on the outer extension and a perforated outlet end positioned within the patient's jejunum;
      2. an inflatable balloon structure mounted around the tube and positioned near the outlet end of the tube;
      3. an inflation valve mounted near the inlet end of the tube;
      4. a valve line connected to the valve and providing an outlet port within the balloon structure, the valve line being positioned adjacent the feeding tube;
      5. a closure plug for the feeding inlet and secured to the feeding tube by an integral band; and,
      6. a locking ring positioned medially along the outer extension of the tube, and sized to frictionally engage the tube and slidably mounted therealong, and adjustable solely by frictional engagement with the tube to accommodate to the size of the wearer, the locking ring providing a plurality of perforations and spaced ridges to enable air circulation between the locking ring and patient's body; whereby,
         i. when the balloon is deflated the feeding tube may be inserted through a stomach placed stoma and into the patient's jejunum;
         ii. when the balloon is inflated through the valve and valve line, it will secure the device within the patient's stomach and form a seal adjacent the stoma;

iii. securement of the ring to the tube being provided solely by frictional engagement therebetween, to secure the device within the patient's body and to prevent undesirable movement of the ring along the tube, whether in the dry state or when lubricated by body fluids, the locking ring being manually adjustable along the tube to accommodate to the size of the patient, and the balloon and ring both functioning to maintain the device in place in the patient;

iv. retraction of the ring being entirely against the force of frictional engagement to enable the stoma and adjacent areas to be cleaned; and, v. when the balloon is deflated, retraction of the ring enables the device to be removed from the patient.

7. The method of claim 6, comprising constructing the device of a medical grade silicone elastomer, and the like.

8. The method of claim 6, comprising surrounding the jejunal tube with a gastrostomy tube, the balloon and locking ring being mounted on the gastrostomy tube, the gastrostomy tube including a feeding inlet and closure plug therefor, the gastrostomy tube being adapted to feed and drain the stomach.

9. The method of claim 6, comprising securing the jejunal tube and gastrostomy tube and their respective inlets by means of a connector.

10. A device for feeding into a patient's jejunum, comprising:

a. an elongate, jejunal feeding tube, including an outer extension from the patient's jejunum, the tube having a feeding inlet end mounted on the outer extension and a perforated outlet end positioned within the patient's jejunum;

b. a flexible plate mounted around the tube and positioned about midway, thereof;

c. a closure plug for the feeding inlet and secured to the feeding tube by an integral band; and, d. a locking ring positioned medially along the outer extension of the tube, and sized to frictionally engage the tube and slidably mounted therealong, and adjustable solely by frictional engagement with the tube to accommodate to the size of the wearer, the locking ring providing a plurality of perforations and spaced ridges to enable air circulation between the locking ring and patient's body; whereby, i. when the feeding tube is inserted through a jejunal placed stoma it will be secured within the stoma by means of the plate which forms a seal with the stoma;

ii. securement of the ring to the tube being provided solely by frictional engaement therebetween, to secure the device within the patient's body and to prevent undesirable movement of the ring along the tube, whether in the dry state or when lubricated by body fluids, the locking ring being manually adjustable along the tube to accommodate to the size of the patient, and the balloon and ring both functioning to maintain the device in place in the patient; and, iii. retraction of the ring against the force of frictional engagement enables the stoma and adjacent areas to be cleaned.

11. The device of claim 10, in which the spaced ridges of the locking ring are arranged radially of the ring.

12. A method for jejunal feeding, comprising:

a. inserting a jejunal tube through a stomach placed stoma and into a patient's jejunum; and, b. supplying food through the tube to the patient's jejunum, the said tube comprising:

1. an elongate, jejunal feeding tube, including an outer extension from the patient's jejunum, the tube having a feeding inlet end mounted on the outer extension and a perforated outlet end positioned within the patient's jejunum;

2. a flexible plate mounted around the tube and positioned about midway, thereof;

3. a closure plug for the feeding inlet and secured to the feeding tube by an integral band; and, 4. a locking ring positioned medially along the outer extension of the tube and slidably mounted therealong, and adjustable solely by frictional engagement with the tube to accommodate to the size of the wearer, the locking ring providing a plurality of perforations and spaced ridges to enable air circulation between the locking ring and patient's body; whereby, i. when the feeding tube is inserted through a jejunal placed stoma it will be secured within the stoma by means of the plate which forms a seal with the stoma;

ii. adjustment of the ring will secure the device to the patient's body by frictional engagement with the feeding tube and prevent the device from being drawn into the patient's stomach; and, iii. retraction of the ring against the force of frictional engagement enables the stoma and adjacent areas to be cleaned.

* * * * *